United States Patent
Alphonse et al.

(10) Patent No.: US 12,404,301 B2
(45) Date of Patent: Sep. 2, 2025

(54) POLYPEPTIDE HAVING ANTI-AGING ACTIVITY, AND APPLICATION THEREOF

(71) Applicant: NANJING ANJI BIOLOGICAL TECHNOLOGY CO., LTD., Nanjing (CN)

(72) Inventors: Joseph Martinez Jean Alphonse, Caux (FR); Hanmei Xu, Nanjing (CN); Dong Wang, Nanjing (CN)

(73) Assignee: NANJING ANJI BIOLOGICAL TECHNOLOGY CO., LTD., Nanjing (CN)

( * ) Notice: Subject to any disclaimer, the term of this patent is extended or adjusted under 35 U.S.C. 154(b) by 184 days.

(21) Appl. No.: 17/767,403

(22) PCT Filed: Jul. 2, 2021

(86) PCT No.: PCT/CN2021/104283
§ 371 (c)(1),
(2) Date: Apr. 7, 2022

(87) PCT Pub. No.: WO2022/022226
PCT Pub. Date: Feb. 3, 2022

(65) Prior Publication Data
US 2024/0067676 A1    Feb. 29, 2024

(30) Foreign Application Priority Data
Jul. 27, 2020    (CN) .................... 202010729862.3

(51) Int. Cl.
*C07K 7/06*  (2006.01)
*A61K 38/00*  (2006.01)
*A61P 39/06*  (2006.01)

(52) U.S. Cl.
CPC ............. *C07K 7/06* (2013.01); *A61P 39/06* (2018.01); *A61K 38/00* (2013.01)

(58) Field of Classification Search
CPC ............ C07K 7/06; A61P 39/06; A61K 38/00
See application file for complete search history.

(56) References Cited

U.S. PATENT DOCUMENTS

| | | | | |
|---|---|---|---|---|
| 10,265,389 | B2 * | 4/2019 | Sugiyama | A61K 38/08 |
| 2004/0006022 | A1 * | 1/2004 | Strominger | A61P 19/02 |
| | | | | 530/328 |
| 2005/0214781 | A1 * | 9/2005 | Macina | C07K 14/47 |
| | | | | 435/325 |
| 2012/0021994 | A1 * | 1/2012 | Sugiyama | C12N 15/113 |
| | | | | 435/6.12 |
| 2013/0143757 | A1 * | 6/2013 | Zhong | G01N 33/6893 |
| | | | | 435/7.1 |

FOREIGN PATENT DOCUMENTS

| | | | | |
|---|---|---|---|---|
| CN | 1242043 | A | 1/2000 | |
| CN | 104402975 | A | 3/2015 | |
| CN | 109206480 | A | 1/2019 | |
| CN | 109232714 | A | 1/2019 | |
| CN | 111793117 | A | 10/2020 | |
| WO | WO-2004044185 | A1 * | 5/2004 | ............. A23K 10/18 |
| WO | WO-2013049830 | A2 * | 4/2013 | ............... C07K 7/06 |
| WO | WO-2014059149 | A1 * | 4/2014 | ......... A61K 31/4192 |

OTHER PUBLICATIONS

Jean Martinez "Unexpected functions of angiotensin converting enzyme, beyond its enzymatic activity," Journal of Peptide Science, Jun. 19, 2017, pp. 1-8.
Balbaa et al. "Secondary substrate binding in aspartic proteinases: contributions of subsites S3 and S'2 to kcat", Archives of Biochemistry and Biophysics, Nov. 1, 1993, pp. 297-303, vol. 306.

* cited by examiner

*Primary Examiner* — Amber D Steele

(57) ABSTRACT

Disclosed is a polypeptide capable of prolonging the lifespan of *Caenorhabditis elegans*, or pharmaceutically acceptable salts thereof. The polypeptide has an amino acid sequence XKFAA SEQ ID NO: 1) (X: any amino acid, preferably T/A). Further, after one or more amino acids on the foregoing polypeptide sequence are deleted, substituted, or added, the resulting polypeptide or the pharmaceutically acceptable salts thereof still have the anti-aging activity. The polypeptide has the effect of prolonging the lifespan of *Caenorhabditis elegans* and anti-aging, and also has the function of enhancing the ability of movement behavior, improving the anti-stress ability, and alleviating the decline of movement ability in the aging process.

5 Claims, 6 Drawing Sheets

Specification includes a Sequence Listing.

```
                        SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: UNSURE
<222> LOCATION: (1)..(1)
<223> OTHER INFORMATION: wherein Xaa is any one or more amino acids or
      acyl

<400> SEQUENCE: 1

Xaa Lys Phe Ala Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthesized

<400> SEQUENCE: 2

Thr Lys Phe Ala Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthesized

<400> SEQUENCE: 3

Ala Lys Phe Ala Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthesized

<400> SEQUENCE: 4
```

```
Pro Pro Thr Thr Lys Phe Ala Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthesized

<400> SEQUENCE: 5

Pro Thr Thr Lys Phe Ala Ala
1               5

<210> SEQ ID NO 6
<211> LENGTH: 6
<212> TYPE: PRT
<213> ORGANISM: Artificial Sequence
<220> FEATURE:
<223> OTHER INFORMATION: Synthesized

<400> SEQUENCE: 6

Thr Thr Lys Phe Ala Ala
1               5

<210> SEQ ID NO 7
<211> LENGTH: 4
<212> TYPE: PRT
<213> ORGANISM: Artificial Sequence
<220> FEATURE:
<223> OTHER INFORMATION: Synthesized

<400> SEQUENCE: 7

Pro Pro Thr Thr
1
```

POLYPEPTIDE HAVING ANTI-AGING ACTIVITY, AND APPLICATION THEREOF

TECHNICAL FIELD

The present invention relates to the field of biophaimaceuticals, and specifically, to a polypeptide having anti-aging activity, and application thereof.

BACKGROUND

Aging is a process in which, after a period of sexual maturity, an organism weakens in self-renewal and repair capabilities of cells, degenerates in structure and function of tissues and organs, and eventually dies. It is characterized by diminished anti-stress ability, disturbance of balance, and increased risk of developing disease. With the aging of the global population, various degenerative diseases of the elderly and the immense medical expenses incurred have become more and more serious social problems. Maintaining the elderly population in healthy state is the key to reducing the social and economic burden brought about by population aging. Therefore, it is of great significance to explore measures and methods for intervening in aging and aging-related diseases that are simple, economical, effective, safe, and suitable for popularization.

In earlier research on aging, scientists believed that pure aging research should be strictly separated from aging-related disease research. Aging-related diseases generally refer to those of which the incidence increases with aging. At present, it is believed that aging-related diseases mainly include cardiovascular diseases, tumors, rheumatism, osteoporosis, cataracts, type 2 diabetes, hypertension, Alzheimer's disease, and the like. However, with the advancement in aging research, it has been found that the occurrence and development of various aging-related diseases are homologous to the aging process, and the aging process itself is the basic risk factor for many aging-related diseases. Social responsibility has also prompted biologists to realize that prolonging lifespan alone cannot reduce the heavy social and economic burden brought about by aging, and only prolonging healthy lifespan has practical significance. Therefore, how to reduce aging-related diseases, improve the quality of life of the elderly in old age, and prolong healthy lifespan has become a hot issue in aging research. At present, there is no strict indicator to measure healthy lifespan. It is generally believed that aging interventions, which can increase the body's anti-stress ability, reduce the occurrence and development of aging-related diseases, and alleviate aging-related degeneration, while prolonging lifespan, can be referred to as prolonging healthy lifespan.

As a classic model animal for aging research, *Caenorhabditis elegans* has the following advantages. First, it has a relatively short lifespan, only 2-3 weeks under standard laboratory conditions, enabling analysis of whole lifespan survival; second, it is easy to obtain a large number of genetically identical animals under controlled ambient conditions; third, its transparent body allows us to directly observe how cells and tissues change with aging; and fourth, an insight into its cells and tissues, neuronal connections, and whole genomes contributes to anti-aging research. A major advantage of the *Caenorhabditis elegans* model is that biological information can be easily provided by genetic methods, thereby determining a large number of genetic mutations that can change lifespan. Finally, the lifespan of *Caenorhabditis elegans* exhibits remarkable plasticity and affected by environmental conditions, nutritional conditions, and genetic mutations. The individual lifespan may change even under controlled conditions, thereby revealing random factors in aging. Therefore, *Caenorhabditis elegans* can be used as a model animal to study the anti-aging activity of drugs.

By far, the prevailing anti-aging is the use of anti-aging drugs. Most of the anti-aging drugs used clinically are synthetic drugs. For example, vitamin E can promote cell division and inhibit the generation of oxygen free radicals, procaine preparations can prolong cell lifespan, and piracetam can delay brain aging; aspirin can delay the decline of body function caused by aging by combating oxidative stress, thereby prolong the lifespan of *Caenorhabditis elegans*; metformin, as an activator of AMP-activated protein kinase (AMPK), can also alleviate cognitive impairment and has a certain effect on delaying aging; and drugs such as PAL-12 (a hexapeptide) and resveratrol analogs are also favored for anti-aging.

SUMMARY

The Sequence Listing created on Mar. 31, 2022 with a file size of 2.00 KB, and filed herewith in ASCII text file format as the file entitled "Sequence_Listing-G204RAYT0007US.TXT," is hereby incorporated by reference in its entirety.

1. Problem to be Resolved

The present invention provides a polypeptide with anti-aging activity, and application thereof. In the present invention, the polypeptide can effectively prolong the lifespan of *Caenorhabditis elegans*, which has a good anti-aging effect and has a great development prospect.

2. Technical Solutions

To resolve the foregoing problem, the technical solutions adopted by the present invention are as follows:

A polypeptide or pharmaceutically acceptable salts thereof is provided, including an amino acid sequence of XKFAA (SEQ IN NO: 1), where X is H-Pro-Pro-Thr-Thr- (SEQ IN NO: 7), H-Pro-Thr-Thr-, H-Thr-Thr-, or any amino acid in a LID form, or acyl such as acetyl or propionyl.

For the polypeptide, X is T or A.

For the polypeptide, the amino acid sequence of the polypeptide is TKFAA (SEQ IN NO: 2) (named Ace) or AKFAA (SEQ IN NO: 3) (named RV1).

Use of the polypeptide in preparing anti-aging and/or life-extending drugs or supplements is provided.

The polypeptide can enhance the ability of movement behavior, improve the anti-stress ability, and alleviate the decline of movement ability in the aging process, thereby prolonging the average lifespan.

When necessary, one or more pharmaceutically acceptable adjuvants may also be added into the foregoing drugs, and the adjuvant includes a diluent, a filler, a binder, a wetting agent, an absorption enhancer, a surfactant, a lubricant, and a stabilizer that are conventional in the pharmaceutical field.

In the present invention, the drugs may be prepared into various forms of injection, freeze-dried powder injection, tablet, or granule. The drugs in various forms may be prepared by conventional methods in the pharmaceutical field.

3. Beneficial Effects

Compared with the prior art, the present invention has the following beneficial effects:

(1) The polypeptide of the present invention has a novel structure with the basic unit of natural amino acids, which is easy to synthesize, separate, and purify;

(2) The polypeptide of the present invention can effectively prolong the lifespan of *Caenorhabditis elegans* and has the anti-aging activity;

(3) The polypeptide of the present invention is safe with week adverse reactions and toxic side effects, does not affect the growth and development of *Caenorhabditis elegans*, and does not affect the reproductive ability of *Caenorhabditis elegans*; and (4) The anti-aging effect of the polypeptide involved in the present invention has good performance in the *Caenorhabditis elegans* model, specifically embodied in significantly improving the ability of movement behavior of *Caenorhabditis elegans*, alleviating the decline of movement ability in the aging process of *Caenorhabditis elegans*, prolonging the time to half death of *Caenorhabditis elegans*, improving the anti-stress ability of *Caenorhabditis elegans*, and prolonging the lifespan of *Caenorhabditis elegans*.

BRIEF DESCRIPTION OF THE DRAWINGS

FIG. 2A shows the results of body length, and FIG. 2B shows the results of body width. The results are expressed as Mean±SEM. Compared with the control group, n.s. represents no significant difference, *p<0.05 represents a significant difference, and **P<0.01 represents a very significant difference. Compared with the control group, the polypeptide groups have no significant difference, indicating that the polypeptides Ace and RV1 do not affect the normal growth and development of *Caenorhabditis elegans*, and the polypeptides are safe.

FIG. 4A shows the results of head swing, FIG. 4B shows the results of body bending, and FIG. 4C shows the results of frequency of pharyngeal pumping. The results are expressed as Mean±SEM. Compared with the control group, n.s. represents no significant difference, *P<0.05 represents a significant difference, and **P<0.01 represents a very significant difference. Compared with the control group, the polypeptide groups have a significant difference, indicating that the Ace and RV1 polypeptides can significantly enhance the muscle movement of *Caenorhabditis elegans* and improve the ability of movement behavior of nematodes.

FIG. 5A shows a survival curve of the experiment on acute heat stress of nematodes on Day 4, and FIG. 5B shows a survival curve of the experiment on acute heat stress of nematodes on Day 8. It can be seen from the figure that the Ace and RV1 polypeptide groups can significantly improve the ability of resistance to acute heat stress of nematodes, indicating that the polypeptide drugs can prolong the life cycle of nematodes in a thermal environment.

FIG. 6A shows the results of rating of the movement ability of nematodes in the experiment on acute heat stress on Day 4, and FIG. 6B shows the results of rating of the movement ability of nematodes in the experiment on acute heat stress on Day 8. It can be seen from the figure that, the proportion of nematodes in grade A in the Ace and RV1 polypeptide groups is higher than that in the control group, indicating that the polypeptide drugs can enhance the ability of resistance to acute heat stress of *Caenorhabditis elegans*, that is, the ability of movement behavior in a thermal environment.

FIG. 7A shows the detection results of the experiment on acute oxidative stress on Day 4, and FIG. 7B shows the detection results of the experiment on acute oxidative stress on Day 8. The results are expressed as Mean±SEM. Compared with the control group, *P<0.05 represents a significant difference, and **P<0.01 represents a very significant difference. It can be seen from the figure that, the survival rate of nematodes in the Ace and RV1 polypeptide groups is significantly higher than that in the control group, indicating that the polypeptide drugs can prolong the life cycle of nematodes in an oxidative environment.

FIG. 8A shows the results of rating of the movement ability of nematodes in the experiment on acute oxidative stress on Day 4, and FIG. 8B shows the results of rating of the movement ability of nematodes in the experiment on acute oxidative stress on Day 8. It can be seen from the figure that, in the experiment on acute oxidative stress on Day 8, the proportion of nematodes in grade A in the Ace and RV1 polypeptide groups is higher than that in the control group, indicating that the polypeptide drugs can enhance the ability of resistance to acute oxidative stress of *Caenorhabditis elegans*; and in the experiment on acute oxidative stress on Day 4, there is no difference in the movement ability between the polypeptide groups and the control group.

FIG. 9A shows the results of rating on the movement ability of nematodes on Day 4, FIG. 9B shows the results of rating on the movement ability of nematodes on Day 8, and FIG. 9C shows the results of rating on the movement ability of nematodes on Day 12. It can be seen from the figure that, compared with the control group, in the Ace and RV1 polypeptide groups on Day 8 and Day 12, the proportion of nematodes in grade A is higher than that in the control group, indicating that the polypeptide can delay the muscle aging of *Caenorhabditis elegans*, and improve the ability of movement behavior of nematodes, thereby prolonging the lifespan of nematodes.

FIG. 10A-B show the results of detection of the movement ability of nematodes on Day 4, FIG. 10C-D show the results of detection of the movement ability of nematodes on Day 8, and FIG. 10E-F show the results of detection of the movement ability of nematodes on Day 12. The results are expressed as Mean±SEM. Compared with the control group,

Figure 1:
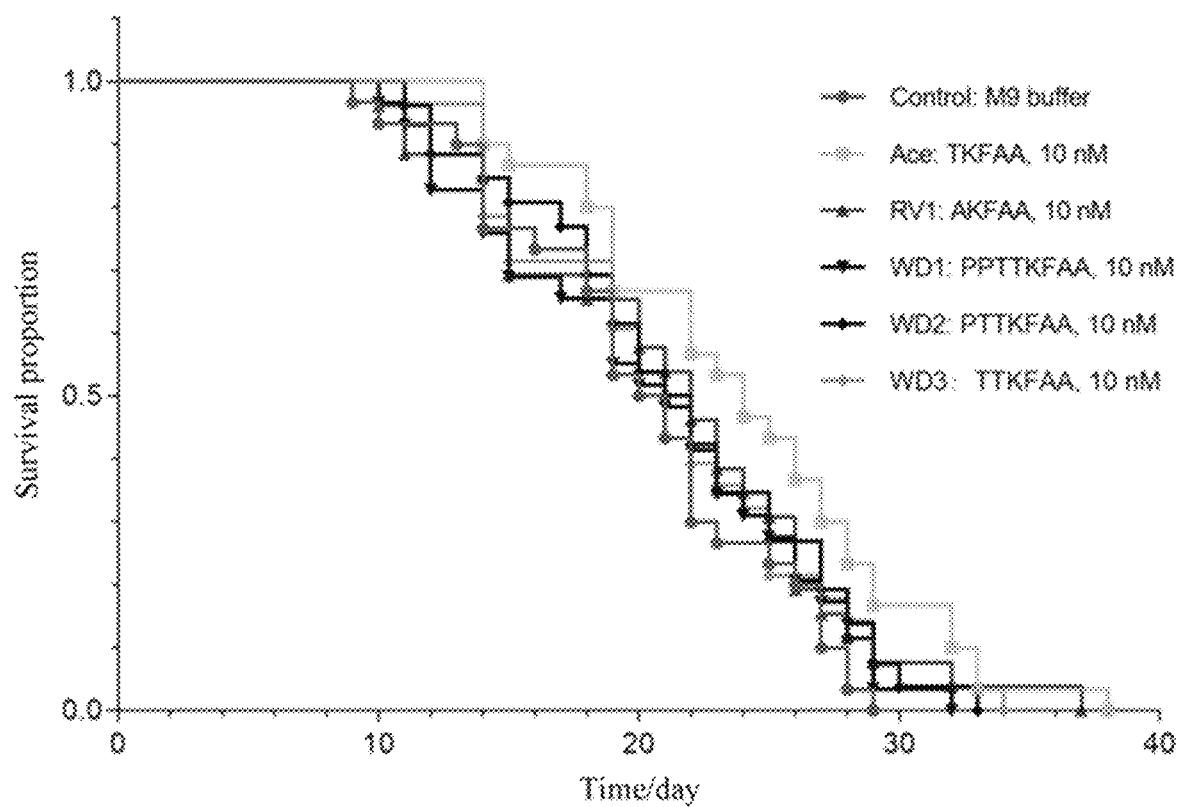
FIG. 1 shows a survival curve of the experiment on the effect of polypeptide on the lifespan of *Caenorhabditis elegans*. It can be seen from the figure that the Ace and RV1 polypeptide groups have the effect of prolonging the lifespan of *Caenorhabditis elegans*.

*P<0.05 represents a significant difference, and **P<0.01 represents a very significant difference. It can be seen from the figure that, compared with the control group, the frequency of head swing in the Ace and RV1 polypeptide groups is significantly higher than that in the control group, and the frequency of pharyngeal pumping on Day 12 is also significantly higher than that in the control group, indicating that the polypeptides can delay the muscle aging of *Caenorhabditis elegans*, improve the ability of movement behavior of nematodes, and alleviate the decline of movement ability of nematodes, thereby prolonging the lifespan of nematodes.

DETAILED DESCRIPTION

The following further describes the present invention with reference to specific examples. The following descriptions are only preferred examples of the present invention, and are not intended to limit the present invention in other forms. Any person skilled in the art may use the technical contents disclosed below to change into equivalent examples with equivalent changes. Any simple modifications or equivalent changes made to the following examples according to the technical essence of the present invention without departing from the content of the solution of the present invention fall within the protection scope of the present invention.

The polypeptide Ace (TKFAA, SEQ ID NO: 2) and polypeptide RV1 (AKFAA, SEQ ID NO: 3) were synthesized by the Engineering Research Center of Synthetic Polypeptide Drug Discovery and Evaluation of Jiangsu Province, with purities of 96.30% and 98.22%, respectively.

EXAMPLE 1

Experiment on the Effect of Polypeptide on the Lifespan of the *Caenorhabditis elegans* model
1. Materials
*E. coli* OP50 cultured at conditions: a shaking incubator, 220 rpm, and 37° C.
Wild-type *Caenorhabditis elegans* cultured at conditions: a constant temperature and humidity incubator, 20° C., and humidity of 45-55%.
5-FUDR: 15.6 μg/mL.
$NaN_3$: 0.4 M.
$H_2O_2$: 30 mM.
Ace: TKFAA (SEQ ID NO: 2), 10 nM.
RV1: AKFAA (SEQ ID NO: 3), 10 nM.
WD1: PPTTKFAA (SEQ IN NO: 4), 10 nM.
WD2: PTTKFAA (SEQ IN NO: 5), 10 nM.
WD3: TTKFAA (SEQ IN NO: 6), 10 nM.
2. Method
Synchronization of *Caenorhabditis elegans*: The NGM plate with a moderate nematode density was selected. The larvae at the L4 stage were picked with a pick needle for about 20 in total and transferred into the blank NGM plate. After they developed into adults and laid the first batch of eggs, all the adults were picked out. About 12 hours later, the eggs hatched into larvae, to obtain the synchronized larvae at the L1 stage.

Preliminary preparation for the experiment on the lifespan of *Caenorhabditis elegans*: The NGM was washed with 1 mL of M9 buffer. The resulting buffer containing the larvae at the L1 stage was collected into an EP tube, placed in a chromatographic cabinet at 4° C. for 5 min, and centrifuged at 1500× g/4° C. for 3 min. The supernatant was removed. After 100 μL of buffer was resuspended, the nematodes were counted under a microscope, and the nematodes were diluted to a concentration of 30 worms/10 μL. 10 μL of diluted nematodes were added into the NGM plate inoculated with *E. coli* OP50, and the nematodes were counted under the microscope to ensure that there were about 30 nematodes. The NGM plate was placed in a constant temperature incubator to culture.

Experiment on the lifespan of *Caenorhabditis elegans*: After the nematodes at the L1 stage developed to the L4 stage, 100 μL of 15.6 μg/mL 5-FUDR was added for inhibition of *Caenorhabditis elegans* from oviposition. After the nematodes developed to adults, the dosing started, and the nematodes were divided into a control group and a 10 nM dose group, which was recorded as day 1 of the lifespan experiment. After that, the dosing was carried out every day, the numbers of nematodes that survived, died, and unexpectedly died were observed and recorded every day, and the status of the nematodes was observed and recorded, until the last nematode died. The criterion for determining whether the nematode died is that *Caenorhabditis elegans* does not respond to strong light or tapping the plate, and does not move at the pharyngeal muscles under a high-power microscope, and finally, the head of the nematode is tapped with a pick needle, if there is still no response, the nematode can be determined as dead. The dead nematodes need to be picked out of the plate. The *E. coli* OP50 needs to be added in time when exhausted. Kaplan-Meier statistical analysis was carried out on the data, and the data results were expressed as Median±SE. Compared with the control group, *P<0.05 represents a significant difference, and **P<0.01 represents a very significant difference.

3. Experimental Results
   (1) The Record of the Results of the lifespan experiment of *Caenorhabditis elegans*

TABLE 1

Recorded results of the number of the remaining *Caenorhabditis elegans*

| Time/day | Number of remaining nematodes in each group | | | | | |
|---|---|---|---|---|---|---|
| | Control | Ace | RV1 | WD1 | WD2 | WD3 |
| 0 | 30 | 30 | 26 | 29 | 26 | 28 |
| 1 | 30 | 30 | 26 | 29 | 26 | 28 |
| 2 | 30 | 30 | 26 | 29 | 26 | 28 |
| 3 | 30 | 30 | 26 | 29 | 26 | 28 |
| 4 | 30 | 30 | 26 | 29 | 26 | 28 |
| 5 | 30 | 30 | 26 | 29 | 26 | 28 |
| 6 | 30 | 30 | 26 | 29 | 26 | 28 |
| 7 | 30 | 30 | 26 | 29 | 26 | 28 |
| 8 | 30 | 30 | 26 | 29 | 26 | 28 |
| 9 | 29 | 30 | 26 | 29 | 26 | 28 |
| 10 | 28 | 30 | 25 | 28 | 26 | 28 |
| 11 | 28 | 30 | 23 | 27 | 25 | 27 |
| 12 | 28 | 30 | 23 | 24 | 23 | 27 |
| 13 | 27 | 30 | 23 | 24 | 23 | 27 |
| 14 | 23 | 27 | 22 | 22 | 22 | 22 |
| 15 | 23 | 26 | 18 | 20 | 21 | 20 |
| 16 | 22 | 26 | 18 | 20 | 21 | 20 |
| 17 | 22 | 26 | 18 | 19 | 20 | 20 |
| 18 | 20 | 24 | 17 | 19 | 18 | 20 |
| 19 | 16 | 20 | 17 | 16 | 16 | 17 |
| 20 | 15 | 20 | 15 | 15 | 14 | 15 |
| 21 | 13 | 20 | 14 | 14 | 13 | 14 |
| 22 | 9 | 17 | 12 | 12 | 11 | 11 |
| 23 | 8 | 16 | 10 | 10 | 9 | 10 |
| 24 | 8 | 14 | 9 | 9 | 9 | 9 |
| 25 | 7 | 13 | 8 | 8 | 7 | 6 |
| 26 | 6 | 11 | 5 | 6 | 7 | 6 |
| 27 | 3 | 9 | 4 | 5 | 5 | 5 |
| 28 | 1 | 7 | 3 | 4 | 3 | 4 |
| 29 | 0 | 5 | 2 | 1 | 2 | 2 |

TABLE 1-continued

Recorded results of the number of the remaining *Caenorhabditis elegans*

| Time/day | Number of remaining nematodes in each group | | | | | |
|---|---|---|---|---|---|---|
| | Control | Ace | RV1 | WD1 | WD2 | WD3 |
| 30 | 0 | 5 | 2 | 1 | 1 | 1 |
| 31 | 0 | 5 | 2 | 1 | 1 | 1 |
| 32 | 0 | 3 | 1 | 0 | 1 | 1 |
| 33 | 0 | 1 | 1 | 0 | 0 | 1 |
| 34 | 0 | 1 | 1 | 0 | 0 | 0 |
| 35 | 0 | 1 | 1 | 0 | 0 | 0 |
| 36 | 0 | 1 | 1 | 0 | 0 | 0 |
| 37 | 0 | 1 | 0 | 0 | 0 | 0 |
| 38 | 0 | 0 | 0 | 0 | 0 | 0 |

Compared with the control group, the day when death occurs in the Ace polypeptide group is delayed, and the longest lifespan of the nematodes is 37 days, 9 days longer than that of the control group. Compared with the control group, the day when death occurs in the RV' polypeptide group has no significant difference, and the longest lifespan of the nematodes is 36 days, 8 days longer than that of the control group. Compared with the control group, the day when death occurs in the WD1, WD2, and WD3 groups also has no significant difference, and the longest lifespans of the nematodes are 31, 32, and 33 days, respectively, 3, 4, and 5 days longer than that of the control group. Refer to Table 1 and FIG. 1 for details.

(2) The Time to Half Death of *Caenorhabditis elegans*

TABLE 2

Detection results of the time to half death of *Caenorhabditis elegans*

| Group | Control | Ace | RV1 | WD1 | WD2 | WD3 |
|---|---|---|---|---|---|---|
| Median survival time/day | 20.000 ± 1.174 | 24.000 ± 2.049* | 22.000 ± 1.525 | 21.000 ± 2.018 | 21.000 ± 1.530 | 21.000 ± 1.323 |
| P value | — | 0.010 | 0.327 | 0.450 | 0.273 | 0.298 |

Note:
The foregoing results are expressed as Median ± SE.
Compared with the control group, *P < 0.05, and **P < 0.01.

Compared with the control group, the time to half death of the Ace group has a significant difference, indicating that the Ace polypeptide has the effect of prolonging the lifespan of *Caenorhabditis elegans* and can prolong the lifespan by 4 days. Compared with the control group, the time to half death of the RV1 group does not have a significant difference, but the time to half death is 2 days longer than that in the control group. Compared with the control group, the time to half death of the WD1, WD2, and WD3 groups does not have a significant difference, and the time to half death is 1 day longer than that in the control group. Based on the above, the Ace and RV1 polypeptide groups have better effects, so that the following anti-aging evaluation experiment is carried out on the Ace and RV1 polypeptides. Referring to Table 2 and FIG. 1 for details, the experimental results are statistically significant.

EXAMPLE 2

Experiment of the Effect of Polypeptide on the Growth and Development of *Caenorhabditis elegans*

1. Materials

The same as that of Example 1.

2. Method

Synchronization of *Caenorhabditis elegans*: The same as that of Example 1.

Experiment on the growth and development of *Caenorhabditis elegans*: The synchronized larvae at the L1 stage were collected and plated on the solid NGM inoculated with *E. coli* OP50. The nematodes were divided into a control group and a 10 nM dose group, and placed in a constant temperature and humidity incubator to culture for 72 h, and the body length and width of the nematodes in the adult stage were detected with a detection method as follows. 20 *Caenorhabditis elegans* were picked from each group and placed on a new solid NGM, and 50 μL of 0.4 M $NaN_3$ was added dropwise. After most of the nematodes were rigid, the nematodes were photographed and recorded under an inverted microscope, and the body length and width of the *Caenorhabditis elegans* were measured with the ruler tool of Photoshop. One-way ANOVAY statistical analysis was carried out on the data, and the data results were expressed as Mean±SEM. Compared with the control group, *P<0.05 represents a significant difference, and **P<0.01 represents a very significant difference.

3. Experimental Results

TABLE 3

Effect of polypeptide on the body length and width of *Caenorhabditis elegans*

| Group | Control | Ace | RV1 |
|---|---|---|---|
| Body length/μm | 1256.974 ± 9.316 | 1255.680 ± 17.447 | 1249.000 ± 14.874 |
| P value (body length) | — | 1.000 | 0.997 |
| Body width/μm | 63.647 ± 0.868 | 63.332 ± 0.964 | 61.763 ± 0.692 |
| P value (body width) | — | 0.999 | 0.549 |

Note:
The foregoing results are expressed as Mean ± SEM.
Compared with the control group, *P < 0.05, and **P < 0.01.

Figure 2A:
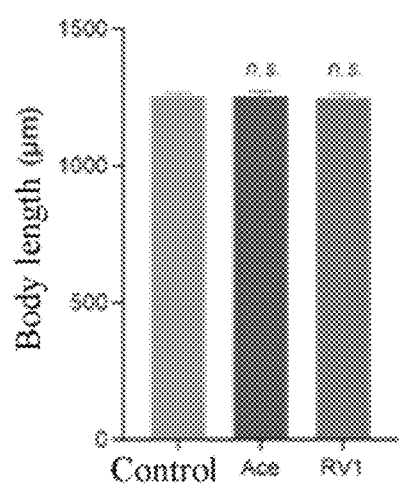
FIG. 2A-2B show results of the effect of polypeptide on the body length and width of *Caenorhabditis elegans*.
Figure 2B:
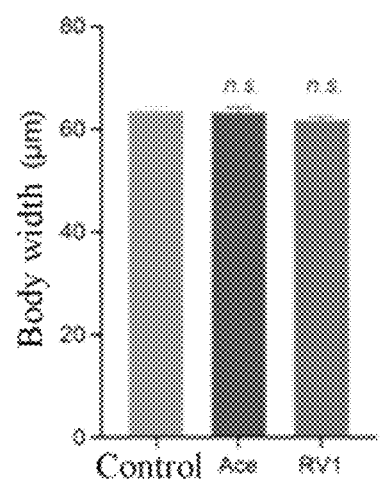

Compared with the control group, the body length and width of *Caenorhabditis elegans* in the polypeptide groups does not have a significant difference, which means that neither Ace nor RV1 polypeptides affect the normal growth and development of *Caenorhabditis elegans*, indicating that these polypeptides are safe. Referring to Table 3 and FIG. 2 for details, the experimental results are statistically significant.

EXAMPLE 3

Experiment of the Effect of Polypeptide on the Reproductive Ability of *Caenorhabditis elegans*
  1. Materials
  The same as that of Example 1.
  2. Method
  Synchronization of *Caenorhabditis elegans*: The same as that of Example 1.
  Detection of the reproductive ability of *Caenorhabditis elegans*: The synchronized larvae at the L1 stage were collected and plated on the solid NGM inoculated with *E. coli* OP50. The nematodes were divided into a control group and a 10 nM dose group, and placed in a constant temperature and humidity incubator to culture to obtain the larvae at the L4 stage. 1 larva at the L4 stage was picked from each group and placed on a new solid NGM. It is ensured that the nematode was transferred to a new medium every day during the egg-laying period. The culture medium containing the eggs was cultured in an incubator for 24 h. The larvae on each plate were counted until the end of egg laying of the nematode. The data was summed up to obtain the total number of offspring of the nematode. The numbers of offspring of 10 nematodes were recorded for each group. One-way ANOVAY statistical analysis was carried out on the data, and the data results were expressed as Mean±SEM. Compared with the control group, *P<0.05 represents a significant difference, and **P<0.01 represents a very significant difference.
  3. Experimental results

TABLE 4

Effect of polypeptide on the number of offspring of *Caenorhabditis elegans*

| Group | Control | Ace | RV1 |
|---|---|---|---|
| Total number of offspring | 289.70 ± 14.827 | 303.80 ± 13.012 | 278.50 ± 15.353 |
| P value | — | 0.947 | 0.977 |

Note:
The foregoing results are expressed as Mean ± SEM.
Compared with the control group, *P < 0.05, and **P < 0.01.

Figure 3:
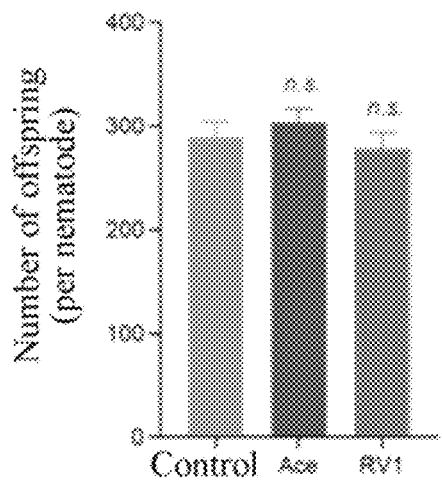
FIG. 3 shows results of the effect of polypeptide on the number of offspring of *Caenorhabditis elegans*. The results are expressed as Mean±SEM. Compared with the control group, n.s. represents no significant difference, *p<0.05 represents a significant difference, and **P<0.01 represents a very significant difference. Compared with the control group, the polypeptide groups have no significant difference, indicating that the polypeptides Ace and RV1 do not affect the reproductive ability of *Caenorhabditis elegans*, and the polypeptides are safe.

Compared with the control group, the total number of offspring of *Caenorhabditis elegans* in the polypeptide groups does not have a significant difference, which means that neither Ace nor RV1 polypeptides affect the reproductive ability of *Caenorhabditis elegans*, indicating that these polypeptides are safe. Referring to Table 4 and FIG. 3 for details, the experimental results are statistically significant.

EXAMPLE 4

Experiment on the Effect of Polypeptide on the Ability of Movement Behavior of *Caenorhabditis elegans*
  1. Materials
  The same as that of Example 1.
  2. Method
  Synchronization of *Caenorhabditis elegans*: The same as that of Example 1.
  Detection of the ability of movement behavior of *Caenorhabditis elegans*: The synchronized larvae at the L1 stage were collected and plated on the solid NGM inoculated with *E. coli* OP50. The nematodes were divided into a control group and a 10 nM dose group, and placed in a constant temperature and humidity incubator to culture for 48 h. Then, the following three indicators of the ability of movement behavior were detected: frequency of head swing, frequency of body bending, and frequency of pharyngeal pumping. For the frequency of head swing, 20 nematodes were picked from each group and transferred to a new and clean culture medium for acclimation for 1 h, a proper amount of M9 buffer was then added, and the number of times the nematode head swings from one side to the other and back within 30 s was observed and recorded under an inverted microscope. For the frequency of body bending, 20 nematodes were picked from each group and transferred to a new and clean culture medium for acclimation for 1 h, the number of times of body bending of the nematode within 30 s was observed and recorded under an inverted microscope, and the distance the nematode crawls forward by one wavelength was recorded as a body bending. For the frequency of pharyngeal pumping, 20 nematodes were picked from each group and transferred to a culture medium inoculated with *E. coli* OP50 for acclimation for 1 h. Under an inverted microscope, it was observed at sufficient magnification to clearly until see the pharyngeal pumping of the nematode, with photographing for 30 s for each nematode, and the number of pharyngeal pumping of the nematode was counted by slow playing video at speed of 0.3 times in PotPlayer. One-way ANOVAY statistical analysis was carried out on the data, and the data results were expressed as Mean±SEM. Compared with the control group, *P<0.05 represents a significant difference, and **P<0.01 represents a very significant difference.
  3. Experimental results

TABLE 5

Effect of polypeptide on the ability of movement behavior of *Caenorhabditis elegans*

| Group | Control | Ace | RV1 |
|---|---|---|---|
| Frequency of head swing/30 s | 56.60 ± 1.690 | 67.65 ± 1.708** | 62.60 ± 1.162* |
| P value (head swing) | — | 0.000 | 0.040 |
| Frequency of body bending/30 s | 12.90 ± 0.397 | 14.85 ± 0.437** | 14.50 ± 0.426* |

TABLE 5-continued

Effect of polypeptide on the ability of movement behavior of *Caenorhabditis elegans*

| Group | Control | Ace | RV1 |
|---|---|---|---|
| P value (body bending) | — | 0.009 | 0.049 |
| Frequency of pharyngeal pumping/30 s | 162.95 ± 2.318 | 189.05 ± 3.891** | 181.10 ± 3.532** |
| P value (frequency of pharyngeal pumping) | — | 0.000 | 0.000 |

Note:
The foregoing results are expressed as Mean ± SEM.
Compared with the control group, *P < 0.05, and **P < 0.01.

Figure 4A:
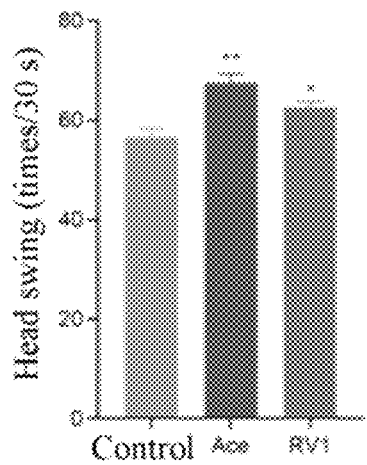
FIG. 4A-4C show results of the effect of polypeptide on the ability of movement behavior of *Caenorhabditis elegans*.
Figure 4B:
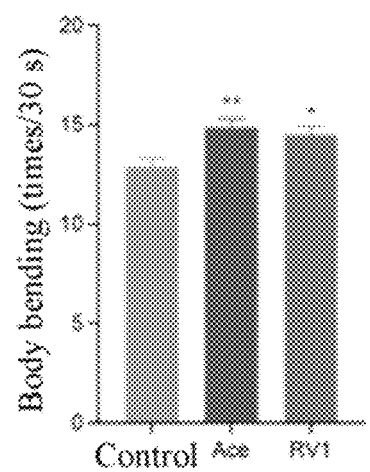
Figure 4C:
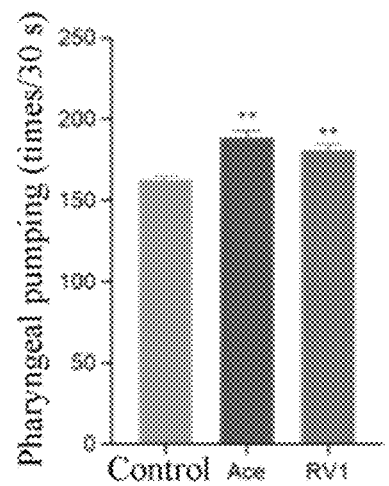
Figure 5A:
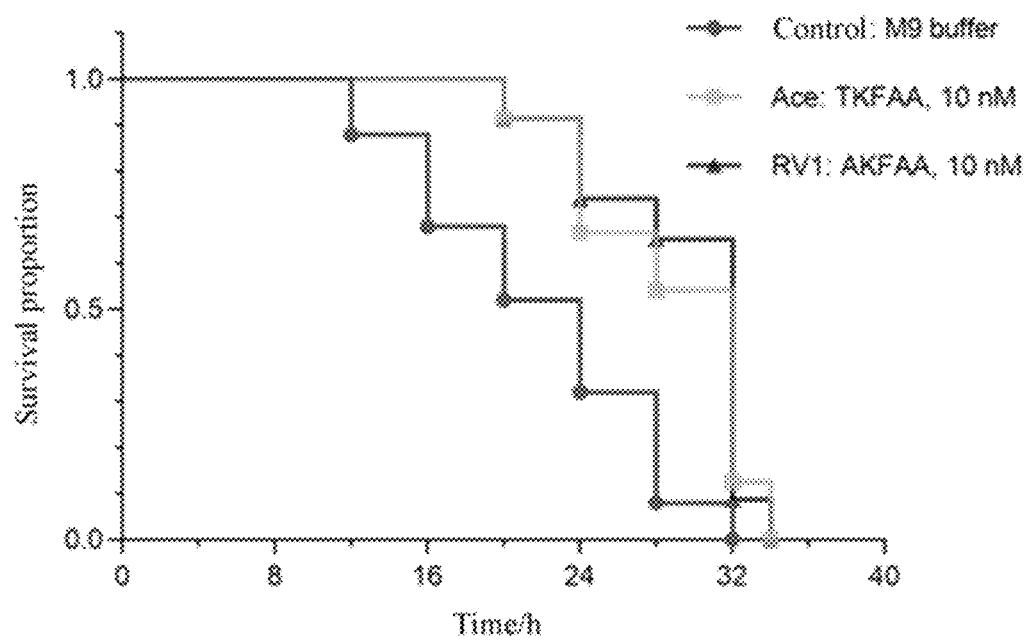
FIG. 5A-5B show a survival curve of the experiment on acute heat stress of *Caenorhabditis elegans*.
Figure 5B:
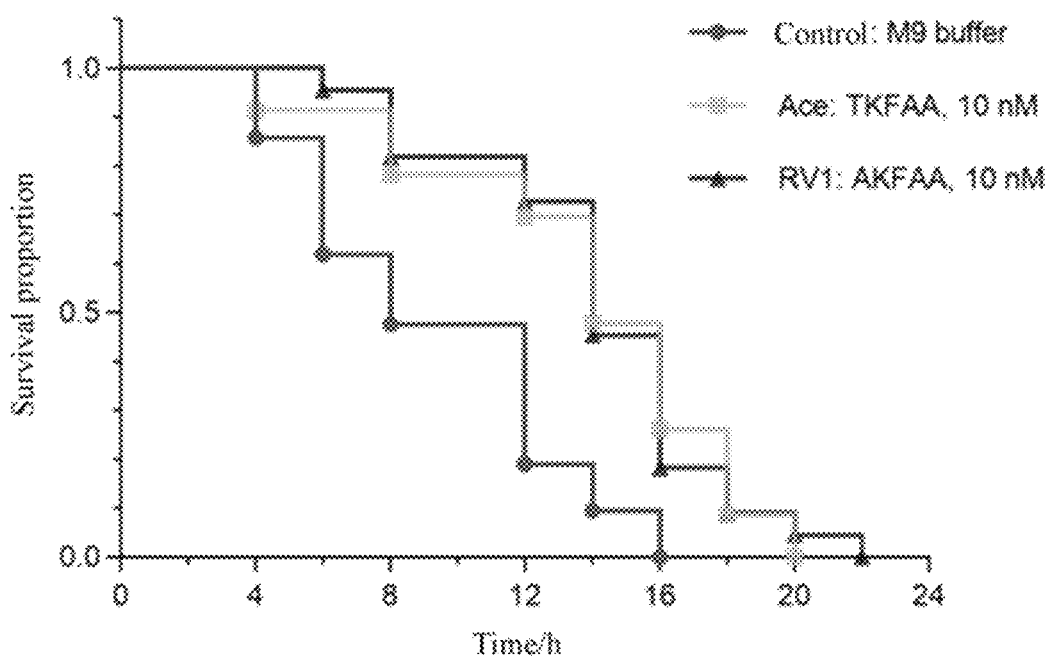
Figure 6A:
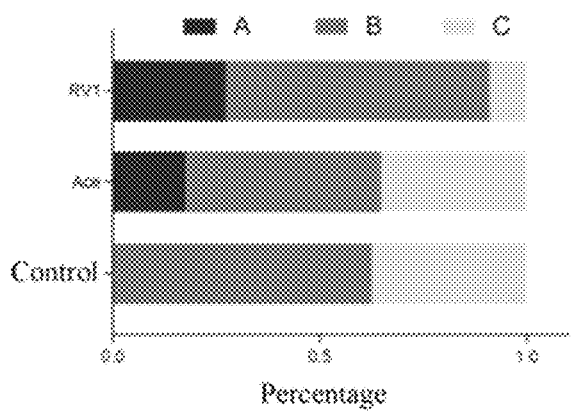
FIG. 6A-6B show the results of rating of the movement ability of *Caenorhabditis elegans* in the experiment on acute heat stress.
Figure 6B:
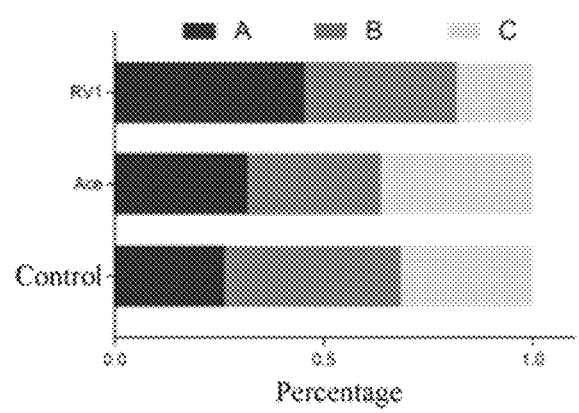
Figure 7A:
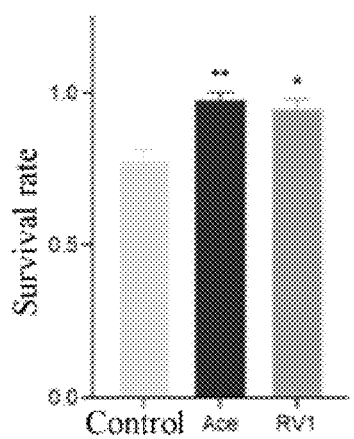
FIG. 7A-7B show the detection results of the experiment on acute oxidative stress of *Caenorhabditis elegans*.
Figure 7B:
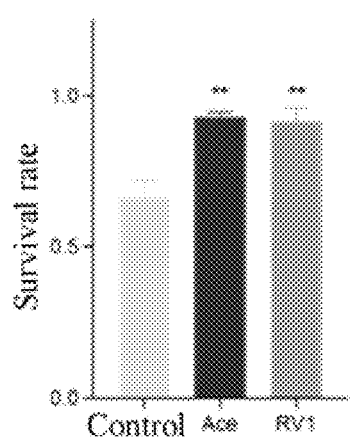
Figure 8A:
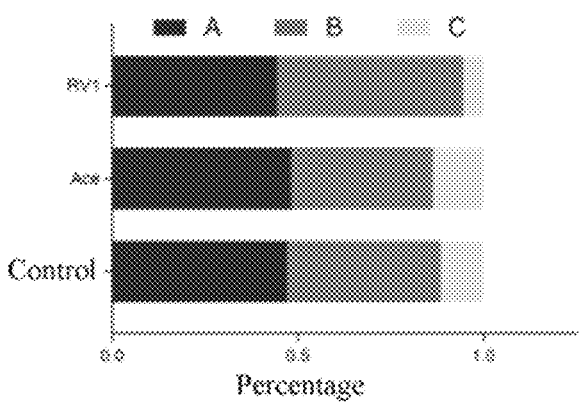
FIG. 8A-8B show the results of rating of the movement ability of *Caenorhabditis elegans* in the experiment on acute oxidative stress.
Figure 8B:
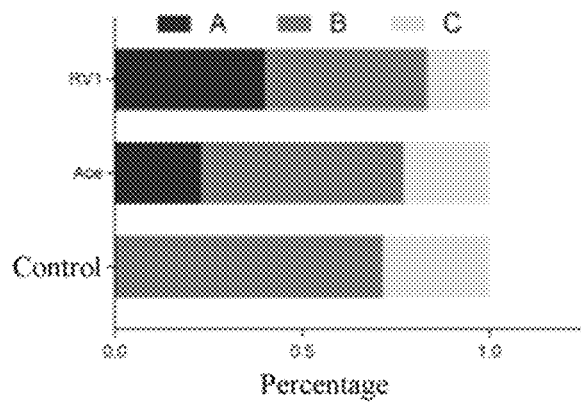
Figure 9A:
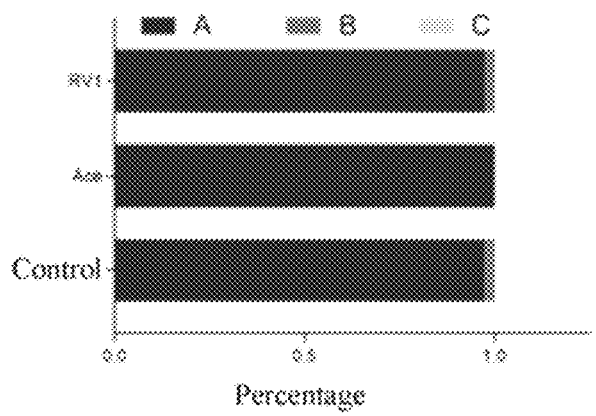
FIG. 9A-9C show the results of rating of the movement ability of *Caenorhabditis elegans* at different ages.
Figure 9B:
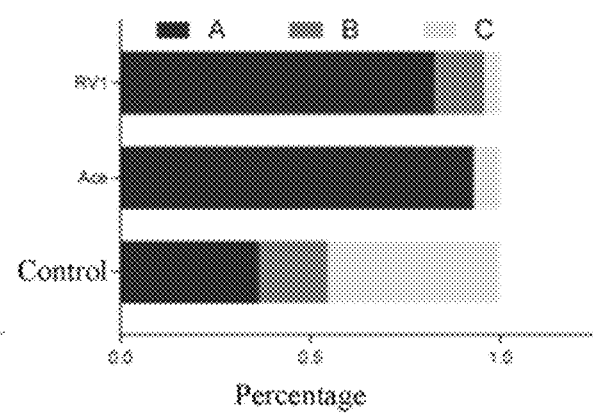
Figure 9C:
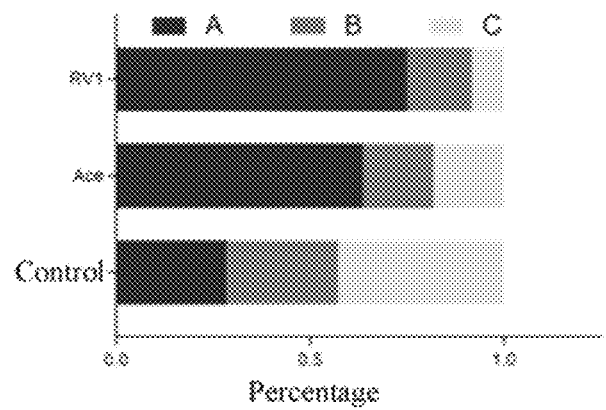
Figure 10A:
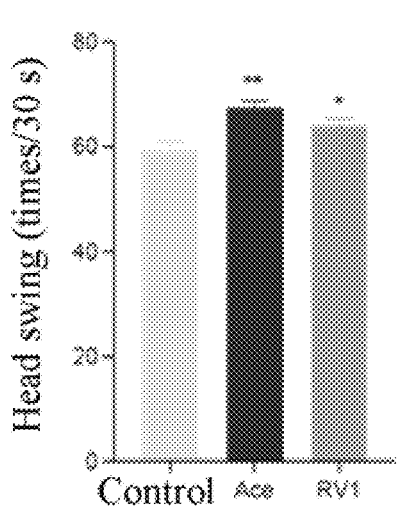
FIG. 10A-10F show the results of detection of the movement ability of *Caenorhabditis elegans* at different ages.
Figure 10B:
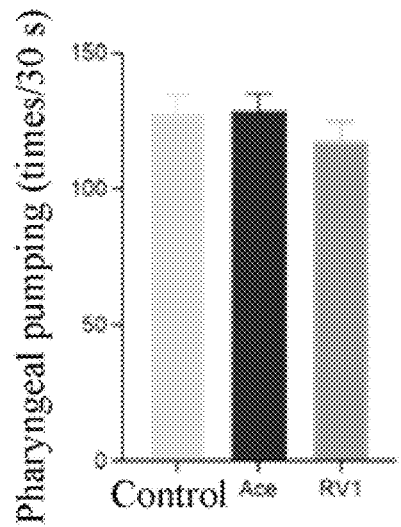
Figure 10C:
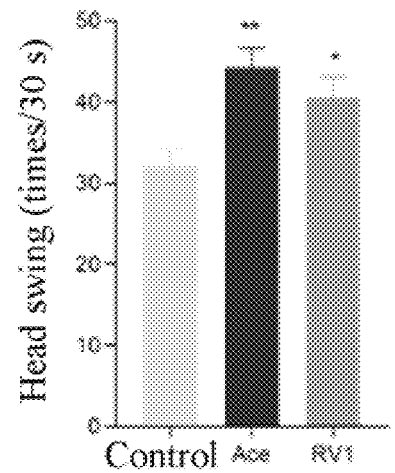
Figure 10D:
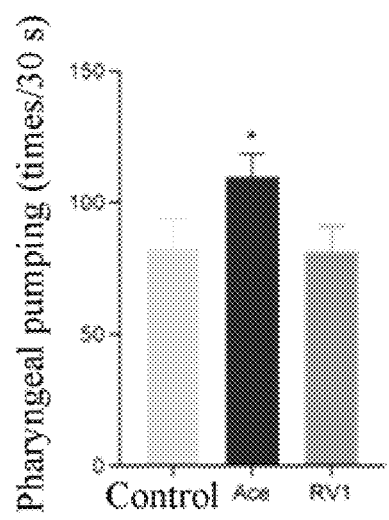
Figure 10E:
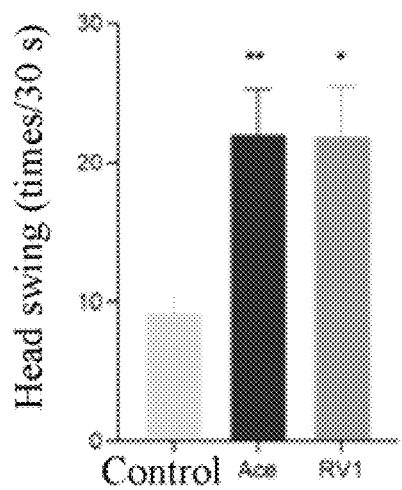
Figure 10F:
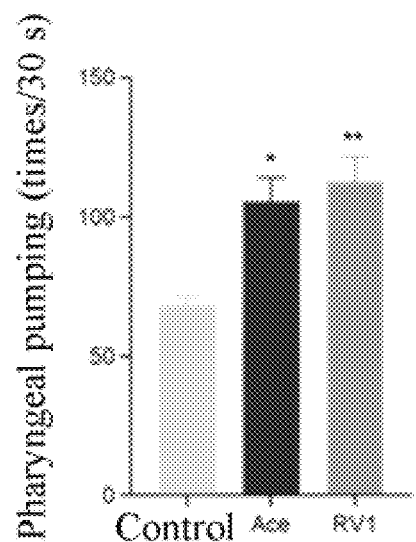

Compared with the control group, the polypeptide groups have a significant difference in the ability of movement behavior of *Caenorhabditis elegans*, indicating that the Ace and RV1 polypeptides can significantly enhance the muscle movement of *Caenorhabditis elegans* and improve the ability of movement behavior of nematodes. Referring to Table 5 and FIG. 4 for details, the experimental results are statistically significant.

What is claimed is:

1. A polypeptide having anti-aging activity consisting of TKFAA (SEQ ID NO: 2), AKFAA (SEQ ID NO: 3), PPTTKFAA (SEQ ID NO: 4), PTTKFAA (SEQ ID NO: 5), or TTKFAA (SEQ ID NO: 6).

2. The polypeptide according to claim 1, wherein each amino acid of the polypeptide is in a D or L form.

3. A method for the preparation of anti-aging drugs or supplements, comprising providing a pharmaceutical composition comprising the polypeptide according to claim 1.

4. The method according to claim 3, wherein one or more pharmaceutically acceptable adjuvants are also added into the pharmaceutical composition comprising the polypeptide, and the adjuvant comprises a diluent, a filler, a binder, a wetting agent, an absorption enhancer, a surfactant, a lubricant, and a stabilizer that are conventional in the pharmaceutical field.

5. The method according to claim 4, wherein the pharmaceutical composition is in the form of an injection, a freeze-dried powder injection, a tablet, or a granule.

* * * * *